Dec. 7, 1965 Q. MANSUINO Plant Pat. 2,577
ROSE PLANT
Filed July 22, 1964
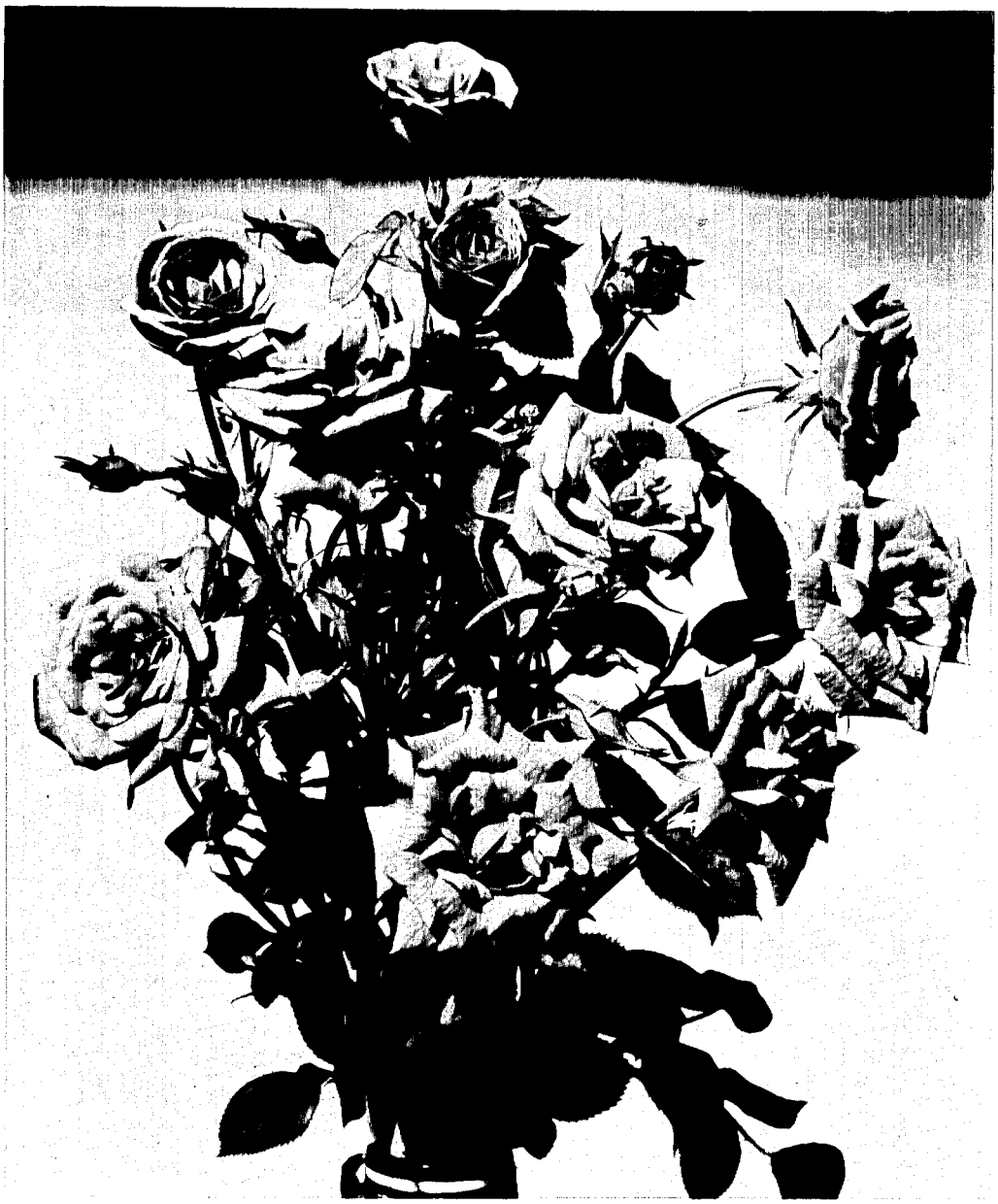
Inventor.
Quinto Mansuino
By: Robb & Robb
Attorneys.

United States Patent Office

Plant Pat. 2,577
Patented Dec. 7, 1965

2,577
ROSE PLANT
Quinto Mansuino, Via Duca d'Aosta 15,
San Remo, Italy
Filed July 22, 1964, Ser. No. 384,565
Claims priority, application Italy, Aug. 23, 1963, 17,295/63
1 Claim. (Cl. Plt.—11)

The present invention relates to a new and distinct variety of rose plant of a class falling between the dwarf or miniature type and the hybrid tea type, which was originated by me in the course of an extended breeding program culminating in the crossing of two unnamed and unpatented varieties respectively identified in my breeding records as Hybrid No. 103 C.G. and Hybrid No. 1896.

Heretofore, many varieties of rose plants now grown for cut flower production are not suitable for other floral use because of their large flower size and other qualities which sometimes present difficulties in the culture and utilization thereof. Accordingly, the primary objective of my breeding program referred to in the foregoing was to produce a new type of rose variety which maintains the overall beauty and harmony of flower shape characteristics of the best cut flower varieties. But with the flowers and stems being of a reduced size in comparison with the usual types, and thus falling in a class between dwarf and hybrid tea types, while bearing the flowers singly to the stem instead of in clusters, and having their shape, growing habit and scent quite similar to those of the large-sized varieties. This objective has been fully achieved in my new variety, along with other desirable features which altogether represent a unique and distinctive combination not found in any other variety known to me, as evidenced by the following characteristics which are outstanding in the new variety:

(1) A shape of the plant, stems, leaves and flowers like those of hybrid tea roses, but harmoniously reduced in size and presenting a more elegant appearance;

(2) Rapid growing and free blooming habits in all seasons of the year, and consequent suitability for both outdoor and greenhouse culture;

(3) Numerous and erect main branches or canes, starting from the base of the plant and bearing numerous, thin, woody, rigid, erect and elegant floral stems having few or no thorns, which produce flowers on thin, rigid and erect peduncles;

(4) Small, light and decorative leaves which clothe the plant and floral stems in an attractive and harmonious manner;

(5) A habit of bearing the flowers single and terminally on the stems, with the flowers ranging from small to medium size;

(6) An urn-shaped flower form on opening, but becoming flat-cupped as the flowers age;

(7) A distinctive and attractive general color tonality of the flowers ranging between Tyrian Purple and Spirea Red;

(8) A delicate but permanent flower fragrance;

(9) Good weather and disease resistance, and especially good resistance to fungus diseases such as, blackspot and mildew;

(10) Good flower shipping qualities;

(11) Very long lasting flower qualities as cut flowers; and

(12) Ease of reproduction by bud grafting and by rooted cuttings.

Asexual reproduction of my new rose variety by bud grafting and by rooted cuttings, as performed by me at Sanremo, Italy, shows that the foregoing characteristics and distinctions come true to form and are established and transmitted through succeeding propagations.

The accompanying drawing shows typical specimens of the vegetative growth and flowers of my new variety in different stages of development and as depicted in color.

The following is a detailed description of my new variety, with color terminology in accordance with Robert F. Wilson's Horticultural Colour Chart, except where general color terms of ordinary dictionary significance are obvious:

Parentage: Seedling.

*Seed parent.*—An unnamed seedling identified as No. 103 C.G.

*Pollen parent.*—An unnamed seedling identified as No. 1896.

Classification: Between dwarf and hybrid tea.

*Plant*

(Observations made from specimens grown outdoors at Sanremo, Italy, during the months of May and June.)

Growing habit: Medium-sized, with spread branches of first and second order, numerous basal shoots, and many floral stems borne on the branches at rather short intervals; the branches are geminate or start in rays, or often in verticils, from the same point of insertion; variable in number; bushy; harmoniously developed.

Average height: From 4 to 5 feet tall from the soil, for plants about two years old industrially grown outdoors.

Roots: Branched; strong; with many little roots deepening in the soil.

Stalk: Variable in length, beyond the stock used for grafting or beyond the length of the cutting used for the reproduction; average length from 6 to 9 inches; average diameter at base from ¾ to 1 inch.

Main branches: Numerous; average from 4 to 10 in number, starting in verticils or at very short intervals from the grafting point on the main stems; ascendent; slightly divergent at their base, then almost vertical and parallel.

*Size.*—Variable; average length from 1 to 1⅓ feet; average diameter at the attachment from ⅝ to ¾ inch.

*Bark.*—Smooth or a little wrinkled; more or less clear brown in colour, with some green tones and sometimes a little scarious on the older branches.

*Thorns.* — Few; scattered; individual; variously shaped and sized; easily detached from the stem; few prickles sometimes present among the thorns; thorns triangular in shape, straight or slightly hooked downwards, and from ⅓ to ½ inch long and from ⅛ to ⅜ inch broad, and from 1/16 to ⅛ inch thick; Hazelnut Brown in colour, with some maroon-green tones. Texture—woody; rigid.

Floral stems: Numerous; average from 16 to 20 in number on each main branch; inserted at short intervals or in verticils on the main branches.

*Shape.*—Thin; cylindrical, woody; erect; rigid; straight, or a little angulated in the nodes, or tortuous; often bearing some little lateral stems inserted like a tuft on the nodes, at the axils of the leaves; the stems are articulated in internodes variable in length on the same stem or from one stem to another, with an average length from ⅝ to 2 inches; floral peduncles differentiated, erect, straight, thin, rigid and from 1½ to 3¼ inches long.

*Nodes.*—Little or moderately differentiated.

*Size.*—Length from 1 to 1⅓ feet; average diameter at the base from ⅛ to ¼ inch; variable from one stem to another.

*Color.*—Ground tissue of Spinach Green, page 187, tones 60/1–2–3, often covered on a side by Maroon, page 185, tones 30–30/1; this color is more diffused on the young stems and turns often to Garnet Brown, page 192, tones 18–18/2.

*Bark.*—Smooth; glabrous; satiny or slightly pruinose, velvety or hairy on the floral peduncles.

*Texture.*—Moderately woody or woody; rigid.

*Thorns.*—Scarce or moderately numerous; more frequent on the lower parts of the stems; scattered individually or in groups of 2 or 3; inserted in each internode; almost absent in the upper part of the stem; flat in shape; triangular; almost regular; with concave sides, with the inferior side more concave, and wtih an acute, differentiated, straight, point; generally perpendicular to the stem, but sometimes a little hooked downward; base of the thorns oval, narrow, and lengthened. Size—from small to medium; generally equal in size on the same stem, but variable from one stem to another; average length from ⅛ to ⅜ inch; average breadth from ⅛ to ¼ inch; average thickness from 1/16 to ⅛ inch. Color—near Garnet Brown, page 192, tones 18/1–2–3. Texture—rigid; resistant; easily detachable from the stem.

Leaves: Numerous; small size; clothe the plant and the stems in light and elegant way; inserted individually on the nodes.

*Growing habit.*—Moderately divergent from the stem, until almost horizontal; often sinuous; bent upward or curved downward in a broad arch.

*Size.*—Increasing from the base of the leaf to the terminal leaflet, as follows: First pair from the base, average length from ½ to ¾ inch, average breadth from ½ to ⅝ inch; second pair from the base, average length from ⅝ to ¾ inch, average breadth from ½ to ⅝ inch; third pair from the base, average length from ⅝ to ¾ inch, average breadth from ½ to ⅝ inch; terminal leaflet, average length from ¾ to ⅞ inch, average breadth from 9/16 to ¾ inch.

*Surface.*—Upper side—smooth; glabrous; moderately glossy; finely wrinkled by pennate veinings in the limb of the leaflets. Under side—glabrous; opaque or slightly velvety; reticulated by pennate veinings moderately salient on the leaflet surface.

*Color.*—Upper side—between Parsley Green, page 193, tones 62–62/1 and Ivy Green, page 200, tones 60/2–3. Under side—near Sage Green, page 198, tones 61–61/1.

*Texture.*—Moderately herbaceous; sometimes more coriaceous; resistant.

*Rachis.*—Sturdy; semi-cylindrical in section; with longitudinal hollow in the upper side; with slightly hairy margins; articulated in 4 or 5 internodes; slightly sinuous or angulated; some slightly or moderately resistant and some triangular prickles hooked downwards are inserted on the under side of the rachis. Color: upper face—Spinach Green, page 187, tones 60/1–2–3, often washed with Maroon, page 185, tones 30/1–2–3; under face—near Sage Green, page 198, tones 67/1–2.

*Flower*

Inflorescence: Terminal flower borne singly on the stem; with small lateral sprouts; generally without floral buds inserted on the upper knots of the stem; peduncle erect, rigid, slightly hairy and with some tender prickles.

Bud: Small; ovoid; much lengthened; with a slender, conic point; bearing foliaceous appendages on the point of the sepals, and others with small lateral appendages divergent from the sides of the sepals and from the bud; sepals open early while the bud continues to grow.

Receptacle and calyx: Regular and elegant; of average size in comparison with the flower; receptacle urn-shaped, having the sepals at its edges.

*Sepals.*—5 in number, opening like a star under the corolla, then curved downwards on the calyx when the blossom ages.

*Shape.*—Triangular; slightly irregular; acute pointed; often prolongated by small foliaceous appendages and with others having thin, lateral, slightly divergent appendages on the sides of the sepals; edges slightly tomentous and slightly irregular.

*Size.*—Moderately variable from one stem to another; average length from ⅝ to 1 inch; breadth at the base from ⅛ to ¼ inch.

*Surface.*—Outside face—smooth; glabrous or slightly granulous. Inside face—lightly tomentous.

*Color.*—Outside face—near Parsley Green, page 187, tones 60–1–2–3, blended with shades of Willow Green, page 199, tones 62–62/1. Inside face—near Sage Green, page 198, tones 61–61/1, blended partially with Willow Green, page 199, tones 62–62/1, and covered by a very short, thin tomentum.

*Texture.*—Average thickness; resistant.

Half-open bud: Almost globular; slightly wider than long; with external edges of the outside petals regularly open; petals being regularly arranged in the corolla; imbricated.

*Average size.*—Length of the flower from base to the apex of the petals from 1 to 1¼ inches; average diameter from 1¼ to 1½ inches.

*Color.*—Between Tyrian Purple, page 159, tone 27 and Spirea Red, page 112, tones 25–25/1 on the open petals of the bud.

Open corolla: Small in size, but harmonious in proportion to the other parts of the plant, stems and leaves; edges slightly irregular and star shaped, with points moderately acute, made by the junctions of the rolls of the lateral edges of the outer petals; profile of the corolla is cup shaped, often formed by the verticils of the petals inserted at a slight distance on the axis of the flower; flat and well developed; central petals regularly arranged in the corolla; imbricated; center concave, with some rudimentary petals in the center of the flower; inner petals well expanded, with edges slightly curved toward the exterior; concave and cup shaped in the center; outer petals cup shaped and well expanded, with lateral edges rolled downward and making points at the meeting of the rolled edges.

*Size.*—Average diameter, when fully open from 1⅝ to 2¼ inches; length of the flower from the receptacle to the apex of the petals from ¾ to one inch.

*General color.*—Between Tyrian Purple, page 159, tones 27–27/1 and Spirea Red, page 112, tones 25–25/1.

*Petals.*—Moderately numerous; from 30 to 40 in number; regularly arranged in the corolla; well displayed; with some rudimentary petals in the center of the flower.

*Shape.*—Oval, with rounded apex, and lateral edges convergent in the attachment at the base; lateral edges smooth; outer edges slightly undulated and sometimes slightly festooned; with some notches moderately deep; small point variously differentiated on the outer edges of the petals; center of the petals cup shaped; outer edges sometimes rolled downward, forming rather obtuse points.

*Attachment.*—Slightly or variously differentiated; sturdy.

*Size.*—Outer petals—average length from 1 to 1¼ inch; average breadth from ⅝ to ¾ inch; size decreasing from the exterior to the interior of the flower. Intermediate petals—average length from ⅝ to ¾ inch; average breadth from ½ to ¾ inch.

*Color.*—Upper side—ground texture Spirea Red, page 112, tones 25–25/1, slightly spotted and blended with Solferino Purple, page 26, tones 26–26/1. Under side—near Tyrian Purple, page 159, tone 27, with light blending of color near Crimson, page 22, tone 22; small area of Lemon Yellow, page 4, tone 4/1 at the attachment, blended in the red of the limb.

*Texture.*—Moderately thick; resistant.

*Surface.*—Upper face—satiny or light velvety. Under face—glabrous; smooth; slightly satiny or opaque.

*Reproductive organs*

Stamens: Moderately numerous; variable in number from one flower to another; average number from 25 to 50.

Filaments: Short; erect; curved toward the center of the flower; white in color, or a little washed with red.

Anthers: Large; oval; biloculated; yellow color.

Styles: Few; average number of 25; erect; straight; approached to their base, then a little more divergent; filiform.

Stigmas: Shower shaped; slightly differentiated at the apex of the styles.

Ovary: Most entirely enclosed in the receptacle; with relatively few seeds.

Hips: Globular; diameter from ½ to ⅝ inch; with persistent sepals.

Scent: Delicate; sweet rose.

Blooming habit: Abundant and continuous in all seasons.

Resistance of the plant to bad weather: Very good.

Disease resistance of the plant: Exceptionally good to blackspot and mildew.

Shipping quality of the flowers: Very good.

Longevity of cut flowers: Very long.

I claim:

A new and distinct variety of rose plant of the class between the dwarf and hybrid tea classes, substantially as herein shown and described, characterized particularly as to novelty by the unique combination of a shape of the plant, stems, leaves and flowers like those of hybrid tea roses, but harmoniously reduced in size and presenting a more elegant appearance, rapid growing and free blooming habits in all seasons of the year, and consequent suitability for both outdoor and greenhouse culture, numerous and erect main branches or canes, starting from the base of the plant and bearing numerous, thin, woody, rigid, erect and elegant floral stems having few or no thorns, which produce flowers on thin, rigid and erect peduncles, small, light and decorative leaves which clothe the plant and floral stems in an attractive and harmonious manner, a habit of bearing the flowers singly and terminally on the stems, with the flowers ranging from small to medium size, an urn-shaped flower form on opening, but becoming flat cupped as the flowers age, a distinctive and attractive general color tonality of the flowers ranging between Tyrian Purple and Spirea Red, a delicate but permanent flower fragrance, good weather resistance, and especially good resistance to fungus diseases such as blackspot and mildew, good flower shipping qualities, very long lasting flower qualities as cut flowers, and ease of reproduction by bud grafting and by rooted cuttings.

No references cited.

ABRAHAM G. STONE, *Primary Examiner.*